US006312434B1

(12) United States Patent
Sutrina et al.

(10) Patent No.: US 6,312,434 B1
(45) Date of Patent: Nov. 6, 2001

(54) DEVICE FOR PRODUCING A SHOCK WAVE TO IMPACT AN OBJECT

(75) Inventors: Thomas A. Sutrina, Rockford; Robert R. Mantell, Arlington Heights; Albert Nowosielski, Roselle, all of IL (US)

(73) Assignee: Northgate Technologies, Inc., Elgin, IL (US)

( * ) Notice: Subject to any disclaimer, the term of this patent is extended or adjusted under 35 U.S.C. 154(b) by 0 days.

(21) Appl. No.: 09/292,104

(22) Filed: Apr. 14, 1999

(51) Int. Cl.[7] .................................................. A61B 17/225
(52) U.S. Cl. ............................................. 606/127; 606/128
(58) Field of Search .................................. 606/127, 128, 606/2.5; 604/22

(56) References Cited

U.S. PATENT DOCUMENTS

| 3,927,675 | 12/1975 | Pohlman et al. . | |
|---|---|---|---|
| 4,030,063 | 6/1977 | Wallen . | |
| 4,095,667 | 6/1978 | Mahig et al. . | |
| 4,227,532 | * 10/1980 | Bluhm et al. ........................ | 128/328 |
| 4,474,180 | 10/1984 | Angulo . | |
| 4,605,003 | 8/1986 | Oinuma et al. . | |
| 4,669,472 | 6/1987 | Eisenmenger . | |
| 4,674,505 | 6/1987 | Pauli et al. . | |
| 4,727,875 | 3/1988 | Dory . | |
| 4,748,971 | 6/1988 | Borodulin et al. . | |
| 4,796,608 | 1/1989 | Koehler . | |
| 4,907,572 | * 3/1990 | Borodulin et al. .................... | 606/128 |
| 5,160,336 | 11/1992 | Favre . | |
| 5,176,688 | 1/1993 | Narayan et al. . | |
| 5,233,972 | 8/1993 | Rattner . | |

(List continued on next page.)

FOREIGN PATENT DOCUMENTS

| 27 24 324 | 8/1978 | (DE) . |
|---|---|---|
| 0 317 507 | 4/1992 | (EP) . |
| 0 806 182 | 11/1997 | (EP) . |
| 455868 | 8/1913 | (FR) . |

OTHER PUBLICATIONS

"Druckluft–Handbuch," published by Vulkan–Verlag Dr. W. Classen Nachf GmbH & Co., Essen, Germany, pp. 282–287 (1971).

"Handbuch Drucklufttechnik," published by VEB Deutscher Verlag fur Grundstoffindustrie, Leipzig, Germany, pp. 176–187 (1986).

(List continued on next page.)

Primary Examiner—Paul J. Hirsch
Assistant Examiner—Michael B. Priddy
(74) Attorney, Agent, or Firm—Brinks Hofer Gilson & Lione

(57) ABSTRACT

The present invention is directed to a device for producing a shock wave to impact an object that includes a transfer member. The device has a voice coil assembly including a permanent magnet and a bobbin member, wherein the permanent magnet provides a first magnetic field. A hammer is attached with the bobbin member; and a coil is operatively attached to the bobbin member, wherein when a voltage is applied to the coil a second magnetic field is generated that opposes the first magnetic field and thereby propels the hammer to contact the transfer member to cause a shock wave to travel along the transfer member. The present invention is also directed to a method for producing a shock wave, that includes the steps of providing a transfer member; providing a voice coil assembly including a permanent magnet and a bobbin member; providing a first magnetic field providing a hammer attached with the bobbin member; providing a coil operatively attached to the bobbin member; and applying a voltage to the coil to generate a second magnetic field that opposes the first magnetic field thereby propelling the hammer to strike the transfer member.

46 Claims, 4 Drawing Sheets

U.S. PATENT DOCUMENTS

| | | | |
|---|---|---|---|
| 5,242,385 | * | 9/1993 | Strukel .................................... 604/22 |
| 5,243,997 | | 9/1993 | Uflacker et al. . |
| 5,281,231 | | 1/1994 | Rosen et al. . |
| 5,449,363 | | 9/1995 | Brust et al. . |
| 5,540,702 | | 7/1996 | Walz . |
| 5,722,980 | * | 3/1998 | Schulz et al. ........................ 606/128 |
| 5,868,756 | * | 2/1999 | Henry et al. ......................... 606/128 |

OTHER PUBLICATIONS

Hans A. von der Mosel, "Eine Einfuhrung in die medizinische Geratrekunde," pp. 104–105, 108–115 (1992).

"Instruction Manual for Lithortron EKL Compact," published by Olympus, pp. 1–26 (1996).

* cited by examiner

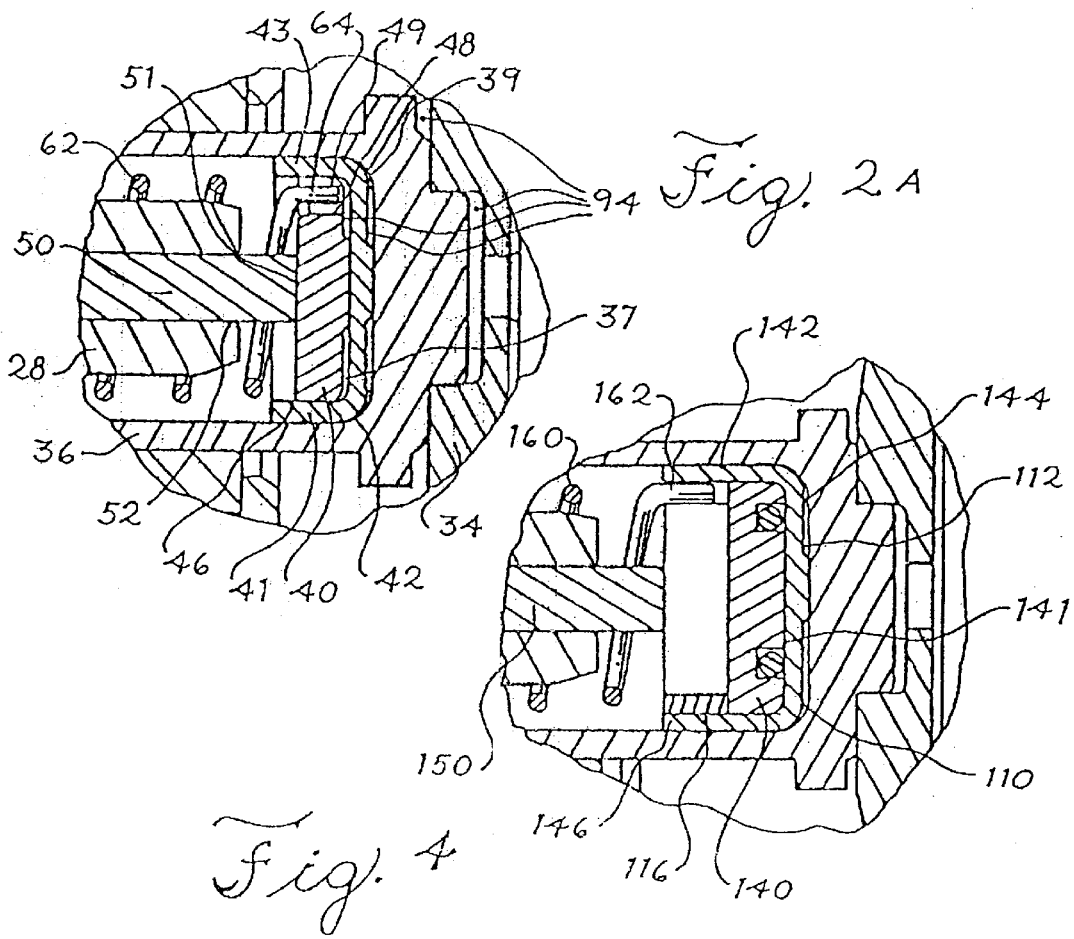
Fig. 2A
Fig. 4
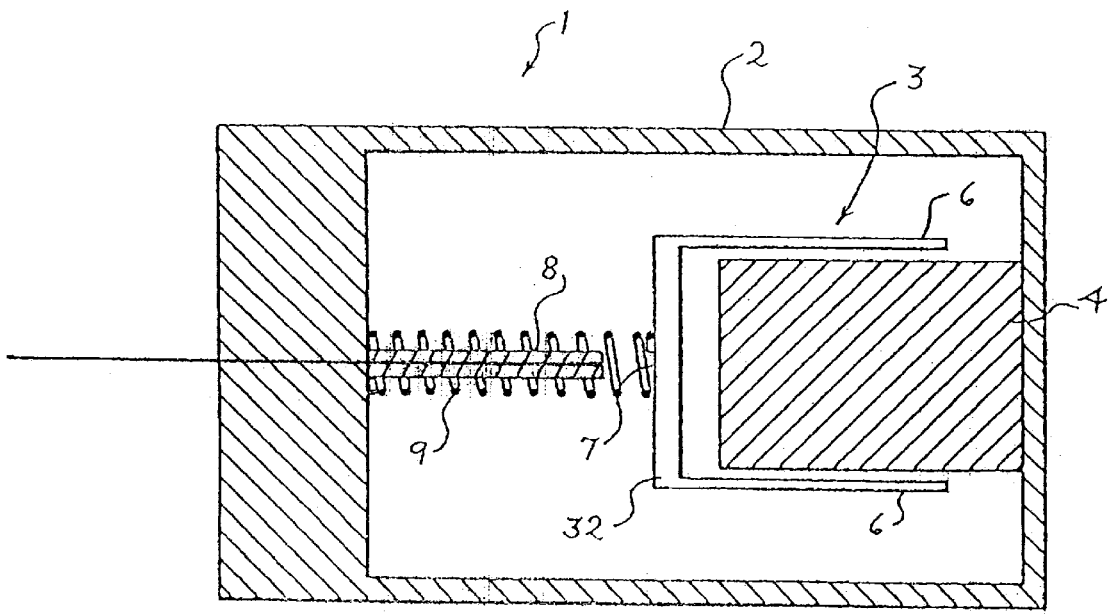
Fig. 5

DEVICE FOR PRODUCING A SHOCK WAVE TO IMPACT AN OBJECT

FIELD OF THE INVENTION

The present invention relates generally to the field of devices for producing shock waves to impact objects and, in particular, to a device and method for crushing stones by a shock wave in the body.

BACKGROUND OF THE INVENTION

Stones or calculi are sometimes formed in organs in the body and their presence can cause significant pain and discomfort to an individual. Such stones often form in the urinary system, in areas such as the kidneys, the urinary tracts and in the bladder. The stones may be removed by surgery or by a procedure that involves using a device to crush the stones into small enough pieces so that they may wash out of the urinary system.

One type of device used to break up stones is commonly referred to as a lithotriptor. A lithotriptor uses a transfer media, such as water, or transfer member, such as a probe, to transfer a shock wave to a stone, thereby crushing the stone. In conventional lithotriptors, a striking member, often referred to as a hammer, is used to impact the transfer member to produce the shock wave. A variety of different apparatuses have been used to propel this hammer against the transfer member. Examples of such devices are shown in U.S. Pat. Nos. 5,160,336, 5,540,702 and 4,727,875.

BRIEF SUMMARY OF THE INVENTION

In a first aspect, the present invention is a device for producing a shock wave to impact an object that includes a transfer member. The device has a voice coil assembly including a permanent magnet and a bobbin member, wherein the permanent magnet provides a first magnetic field. A coil is operatively attached to the bobbin member, wherein when a voltage is applied to the coil a second magnetic field is generated that opposes the first magnetic field and thereby propels the bobbin member to contact the transfer member to cause a shock wave to travel along the transfer member.

Further in this aspect of the invention there may be provided a bobbin member comprised of a non-magnetic material, a voice coil assembly that has a hammer comprised of a non-magnetic material to contact the transfer member, a cup positioned inbetween and operatively attached to the bobbin member and the hammer, an o-ring positioned between the hammer and the cup, a transfer member that is a probe, a biasing member to bias the bobbin member in a first position and, a power source operatively attached to the device, the power source being a battery. Also in this aspect, a portion of the bobbin member may be disposed around the permanent magnet when the bobbin member is in a first position.

In a second aspect, the present invention is a device for producing a shock wave to impact an object, that includes a housing having an exit end; a transfer member operatively attached to the exit end of the housing; a hammer movable from a rest position to a second position, wherein when the hammer is in the second position the hammer impacts the transfer member to produce a shock wave that travels along the transfer member; and a battery to power the device.

Further, in this aspect the hammer may be operatively attached to a bobbin member, the bobbin member may be comprised of a non-magnetic material, the hammer may be comprised of a non-magnetic material and the transfer member may be a probe. Also in this aspect there may be provided a cup positioned inbetween and operatively attached to the bobbin member and the hammer, an o-ring positioned between the hammer and the cup and a biasing member to bias the bobbin member in a first position.

In a third aspect, the present invention is a device for producing a shock wave to impact an object that includes a housing having an exit end; a transfer member operatively attached the exit end of the housing; a permanent magnet disposed within the housing proximate the magnet end to provide a first magnetic field; a magnetic field generating member spaced apart from the permanent magnet; and a hammer fixed with the magnetic field generating member, the magnetic field generating member operative to provide a second magnetic field that opposes the first magnetic field to propel the hammer to strike the transfer member thereby causing a shock wave to travel along the transfer member.

Further in this aspect, the magnetic field generating member may be comprised of a non-magnetic material, the hammer may be comprised of a non-magnetic material, the biasing apparatus may be an o-ring and the transfer member may be a probe.

Also in this aspect, there may be a cup positioned inbetween and operatively attached to the magnetic field generating member and the hammer, a biasing apparatus positioned between the hammer and the cup, a biasing member to bias the magnetic field generating member in a first position and a power source operatively attached to the device, the power source being a battery. In addition, the magnetic field generating member may be a bobbin.

In a fourth aspect, the present invention is a device for producing a shock wave to impact an object that includes a housing having a magnet end and an exit end, the exit end defining an opening; a probe attached to the housing and extending through the opening; a permanent magnet disposed within the housing proximate the magnet end; a bobbin member located intermediate the permanent magnet and the probe; the bobbin member movable between a first position and a second position; a coil operatively attached to a portion of the bobbin member; and a hammer positioned intermediate the bobbin and the probe, wherein passing an electrical current through the coil results in the bobbin member moving from a first position to a second position causing the hammer to strike the probe, thereby causing a shock wave to travel through the probe.

Further in this aspect, the bobbin member may be comprised of a nonmagnetic material and the hammer may be comprised of a non-magnetic material. Also in this aspect there may be provided a cup positioned inbetween and operatively attached to the bobbin member and the hammer, an o-ring positioned between the hammer and the cup, a biasing member to bias the bobbin member in a first position and a power source operatively attached to the device, the power source being a battery.

In a fifth aspect, the present invention is a device for producing a shock wave to impact an object that includes means for transferring a shock wave to an object; means for providing a first magnetic field; means for generating a second magnetic field to oppose the first magnetic field; and means for impacting the means for transferring, the means for impacting being operatively attached to the means for generating so that when the second magnetic field is generated the means for impacting strikes the means for transferring to produce a shock wave.

In a sixth aspect, the present invention is a method for producing a shock wave, that includes the steps of providing a transfer member; providing a voice coil assembly including a permanent magnet and a bobbin member; providing a first magnetic field providing a hammer attached with the bobbin member; providing a coil operatively attached to the bobbin member; and applying a voltage to the coil to generate a second magnetic field that opposes the first magnetic field thereby propelling the hammer to strike the transfer member.

In a seventh aspect, the present invention is a device for producing a shock wave to impact an object, including a housing having an exit end; and a transfer member operatively attached to the exit end of the housing. The device includes a hammer movable from a rest position to a second position, wherein when the hammer is in the second position the hammer impacts the transfer member to produce a shock wave that travels along the transfer member; and a power supply, supplying a voltage in the range of about 12–57 volts.

In an eighth aspect, the present invention is a device for producing a shock wave to impact an object, including a housing having an exit end; and a transfer member operatively attached to the exit end of the housing. The device includes a hammer movable from a rest position to a second position, wherein when the hammer is in the second position the hammer impacts the transfer member to produce a shock wave that travels along the transfer member; and a power supply, supplying a voltage of less than about 48 volts.

The invention provides the foregoing and other features, and the advantages of the invention will become further apparent from the following detailed description of the presently preferred embodiments, read in conjunction with the accompanying drawings. The detailed description and drawings are merely illustrative of the invention and do not limit the scope of the invention, which is defined by the appended claims and equivalents thereof.

BRIEF DESCRIPTION OF SEVERAL VIEWS OF THE DRAWINGS

FIGS. 2 & 2A are views of the embodiment shown in FIG. 1, when a bobbin is in a second position.

FIG. 4 is an exploded view of a portion of the invention shown in FIG. 3.

FIG. 5 is a cross sectional schematic view of an embodiment of the present invention.

DETAILED DESCRIPTION OF THE INVENTION

Figure 1:
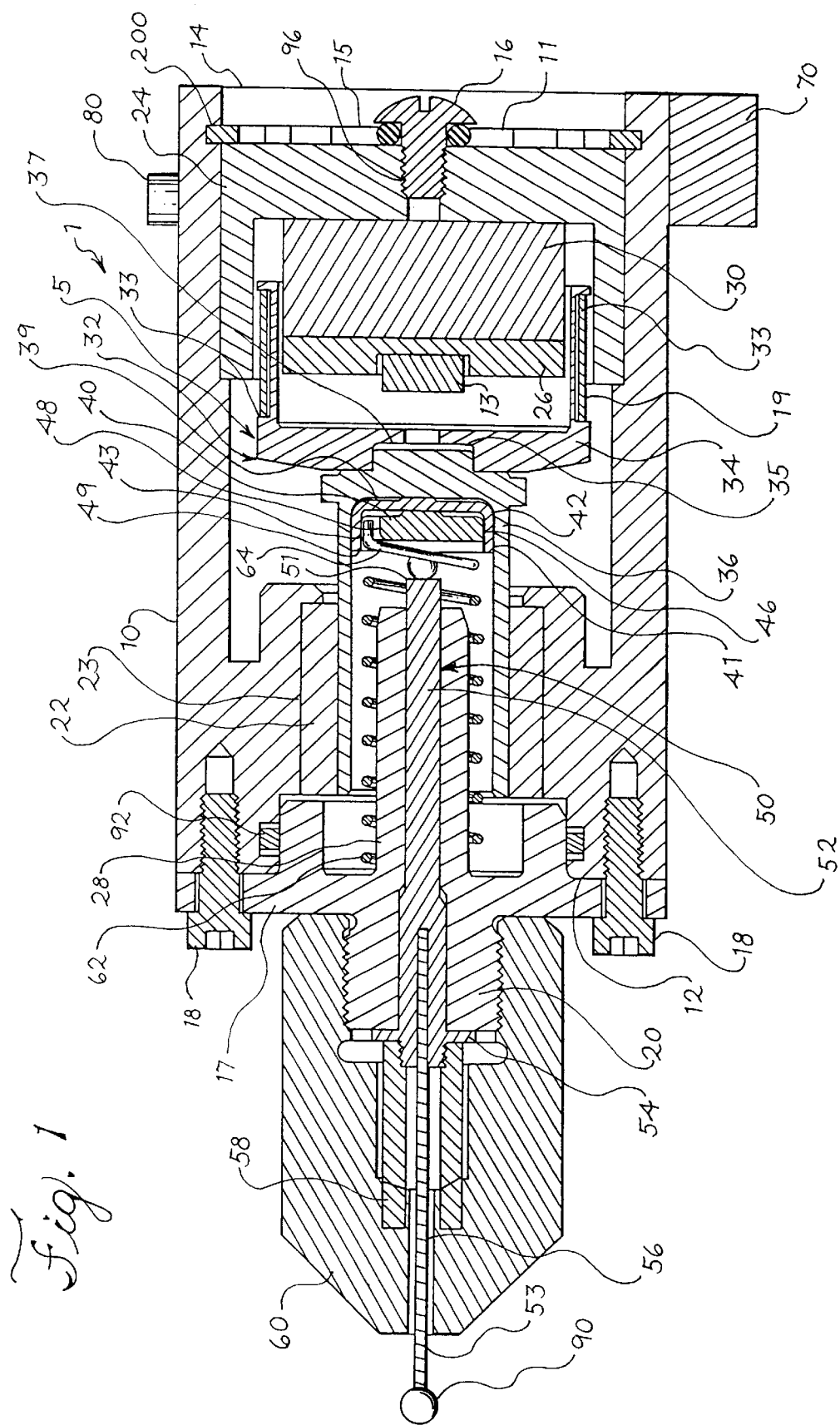
FIG. 1 is a cross sectional view of an embodiment of the present invention when a bobbin is in a first position.

Referring to FIG. 5 there is generally disclosed a device 1 for producing a shock wave to impact an object. Generally, the device 1 comprises an outer housing or shell 2. Within the housing there is located a voice coil 3, which comprises a permanent magnet 4, a bobbin 32 and a coil 6 (not shown in detail). The bobbin also may have a striking surface or hammer 7. The device further has a probe or wire 8. The device may further comprise a return spring 9. Generally, in operation an electric current is applied to the voice coil resulting in the coil moving toward the probe. The striking surface of the coil then strikes the probe, which is also in contact with the object to be crushed. The force from the voice coil striking the probe is transmitted though the probe to the object to be crushed. The return spring then forces the voice coil back away from the probe.

Several variation of this design are disclosed and described below. These are provided by way of example and are illustrative and not intended to be limiting.

Referring to FIG. 1, there is shown an embodiment of a device to produce a shock wave to impact an object, such devices may also be referred to as a lithotriptor 1. The lithotriptor 1 includes a housing 10. Disposed within the housing is a voice coil assembly 5 that includes a permanent magnet 30 and a bobbin member or bobbin 32. A coil 19 is wrapped around a portion of the bobbin 32 and a hammer 40 is attached with part of the bobbin 32. Extending out of the housing is a transfer member or probe 50 that can make contact with a stone to transfer a shock wave to the stone.

The housing 10 may be sized and shaped to accommodate the voice coil assembly 5 and the transfer member or probe 50. Referring to FIGS. 1 and 2A, in a preferred embodiment, as shown in FIG. 1, the housing has an exit end 12 and a magnet end 14 formed opposite the exit end 12. A retaining ring 15 is held in position in a groove 200 of the housing 10 to prevent a cup pole 24 from moving. A screw 16 passes through an o-ring 11 and screws into a threaded hole 96 disposed in the cup pole 24. A longer screw (not shown) may be inserted into the threaded hole 96 in order to withdraw the magnet. An end o-ring 11 seals the permanent magnet 30 from the atmosphere. An adhesive is preferably used to align the permanent magnet 30 with the cup pole 24 and a disk pole 26 to form a concentric assembly. A rubber bumper 13 is bonded to the disk pole 26. The rubber bumper 13 prevents the bobbin 32 from hammering the disk pole 26.

Referring again to FIG. I inner walls 23 of the housing 10 extend inward adjacent a journal bearing 22. The journal bearing 22 is disposed concentrically around a second portion 36 of the bobbin 32 to position and guide the bobbin 32. A front plate 17 is preferably attached to the exit end 12 of the housing 10 using front screws 18. An o-ring seal 92 is disposed between the inner walls 23 and the front plate 17 to prevent leakage. The housing may be made from any material that is strong enough to hold the component parts in place during use. For example it may be made of metals, such as steel or aluminum, plastic and or combinations of these materials. Alternatively, the housing could be formed in a variety of different shapes and be comprised of a number of various materials. For example the inside surface of the housing could be sized and shaped to accommodate the voice coil assembly 5 and probe 50 where as the outside surface could be shaped to mold to a persons hand. The housing could be elliptical shaped, barrel shaped, conical shaped or oblong shaped. Additionally, the outside of the housing, the part that is held by the user could be made from a different material than the inside of the housing. Thus, the outside material could be select for feel, grip and ease of cleaning, while the inside material could be selected for strength.

In a preferred embodiment, an inner sleeve 28 is formed in the front plate 17 and extends towards the magnet end 14. The inner sleeve 28 is designed to hold a portion of the probe 50 in place. Also formed in the front plate 17 is a threaded member 20 that is sized to accommodate a cap 60.

In a preferred embodiment, the permanent magnet 30 is positioned proximate the magnet end 14 of the housing. The permanent magnet 30 is preferably located and held inbetween the cup pole 24 and the disk pole 26. In a preferred embodiment, the permanent magnet 30 is cylindrical shaped and is rectangular shaped in cross section (as viewed from FIG. 1). The permanent magnet 30 provides a first magnetic field that is oriented generally towards the exit end 12 of the housing 10. Alternatively, the permanent magnet 30 could have a variety of cross sectional shapes, such as elliptical, circular, or trapezoidal. Further, instead of being a separate element, the permanent magnet 30 could be formed as part of the housing. Further, two or more permanent magnets could be used to provide a first magnetic field. Instead of using a permanent magnet, other sources of providing a first magnetic field could be used such as an electromagnet.

Figure 2:
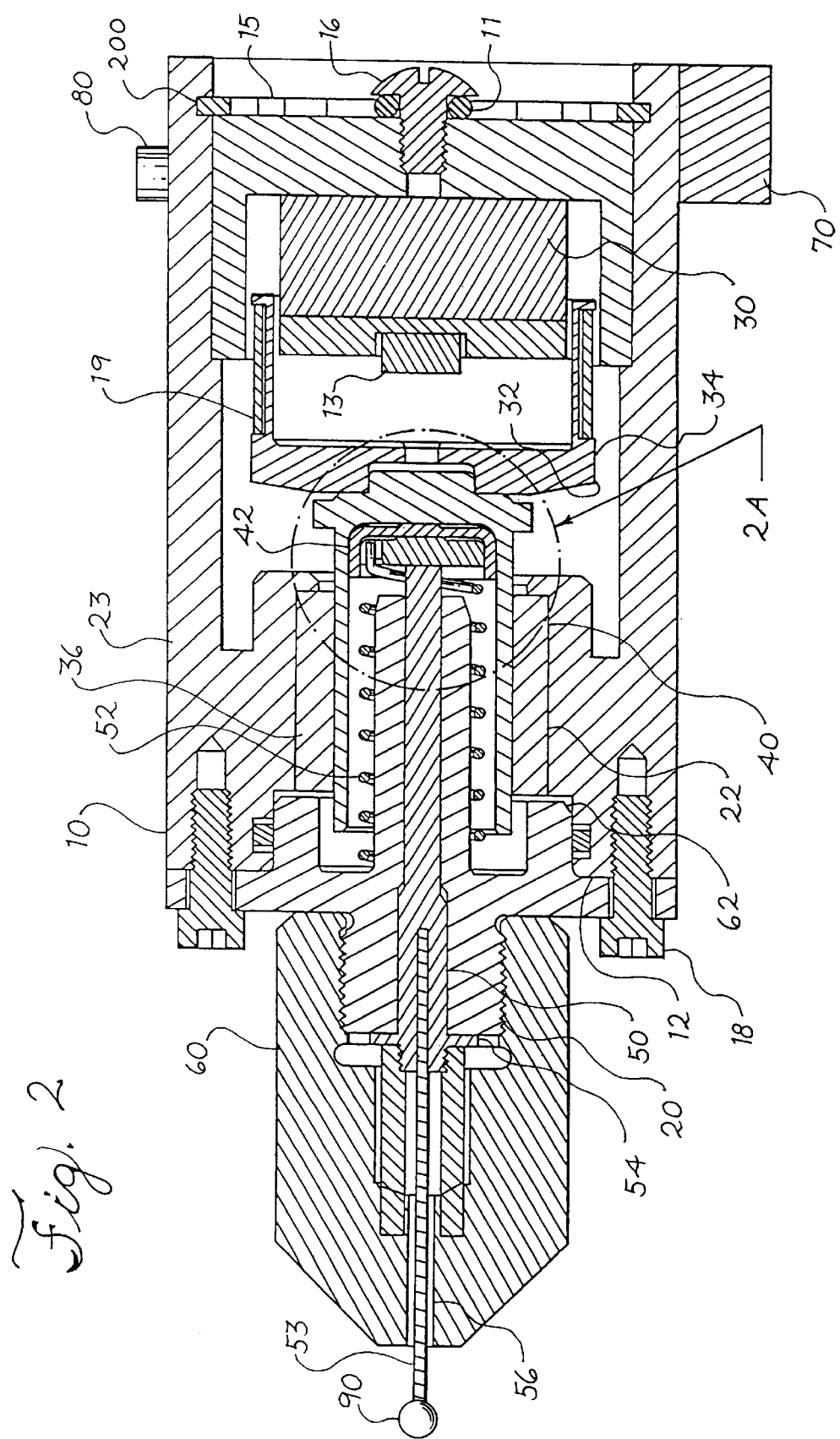

As shown in FIGS. 1 and 2 a bobbin 32 is located inbetween the exit end 12 and the magnet end 14 and is movable between a first position and a second position. The bobbin 32 is preferably comprised of a first portion 34 and a second portion 36.

Referring to FIG. 1, the first portion 34 generally opens in the direction of the permanent magnet. The first portion 34 includes a grooved portion 33 that in part extends along the permanent magnet. The grooved portion 33 is sized and shaped to accommodate the coil 19. A receiving surface 35 is formed on the first portion 34 of the bobbin 32 proximate the exit end 12. The receiving surface 35 is sized and shaped to accommodate a top member 37 of the second portion 34.

Referring to FIGS. 1 and 2A, in a preferred embodiment, the second portion 36 is attached to the first portion 34. The two portions 34,36 are preferably attached by positioning the top member 37 into the receiving surface 35 formed on the first portion 34. In a preferred embodiment the interface between the top member 37 and the receiving surface 35 forms a press fit. Alternatively, an adhesive may be applied in a space 94 located between the top member 37 and the receiving surface 35 to glue the top member 37 to the receiving surface 35. Also, the first portion 34 and second portion 36 could simply be glued together using some type of adhesive and without using a top member 37. In still another embodiment, the bobbin 32 could be formed as one piece instead of two portions 34, 36. In another embodiment holes (not shown) may be formed in the top member 37 to allow air to pass through.

The second portion 36 of the bobbin 32 also is preferably generally "U" shaped, opens around the sleeve 28 and is disposed within and adjacent to the journal bearing 22. In an alternative embodiment, the bobbin 32 could be formed as one piece instead of two portions 34, 36. The first portion 34 and second portion 36 are preferably made of a non-magnetic material such as aluminum, brass, titanium, stainless steel, nickel, beryllium, magnesium or inconel. Alternatively, the bobbin 32 may be made of a nonconductive material or out of a conductive material that is insulated. In another alternative embodiment, a split or gap may be formed in the bobbin 32 to prevent a shorted turn.

Referring to FIGS. 1 and 2A, a cup 42 having a first wall 41 and a second wall 43 is attached inside the second portion 36 to an end 39 of the second portion 36. In a preferred embodiment the cup is attached to the second portion 36 by being press fit into the end 39 of the second portion 36. A space 94 may be disposed between the cup 42 and the end 39 and adhesive may be disposed in this space 94. The cup is generally "U" shaped and is sized so that the first wall 41 and the second wall 43 are adjacent the interior of the second portion 36. In an alternative embodiment, the cup 36 could be press fit to the second portion 36. The cup 42 is preferably made of hard plastic. Alternatively, the cup could be made of any ceramic or composite fiber material.

The cup 42 acts in part as an insulator between the bobbin 32 and the hammer 40. Alternatively, the cup 42 could be removed, for example where a ground fault interrupter circuit was used in conjunction with the device thereby preventing the need for such an insulator.

Referring again to FIGS. 1 and 2A, a hammer 40 having a first edge 46 and a second edge 48 is positioned against the cup 42. In a preferred embodiment the hammer 40 is fixed to the cup using a press fit and glue. A space 94 may be disposed between the cup 42 and the hammer 40 and adhesive may be disposed in the space 94. The hammer is generally cylindrical shaped and is rectangular shaped in cross section (as viewed from FIG. 1) and sized so that the first edge 46 is adjacent the first wall 41 of the cup and so that the second edge 48 is proximate the second wall 43, thus forming a gap 49 between the second edge 46 and the second wall 43. In a preferred embodiment the hammer is made of a hard metal such as steel, aluminum, brass, titanium, stainless steel or nickel. Alternatively, the voice coil assembly itself could be formed with, reinforced, or hardened to form a striking surface. In another alternative embodiment, the hammer 40 may be fixed directly to the second portion 36 without the use of an intervening cup 42. Alternatively, the hammer may be free floating, such as a slug or ball bearing or partially free floating.

A biasing member or spring 62 is positioned to extend from the exit end 12 of the housing 10 to the cup 42. The spring has an upper member 64. The upper member 64 is disposed in the gap 49 and makes contact with the cup 42. The spring 62 biases the bobbin 32 towards the magnet end 14 of the housing 10. The spring is preferably made of spring steel. Alternatively, the spring could be made of an elastomeric type material such as rubber or silicone. In an alternative embodiment electromagnetic, pneumatic or mechanical means could be used to return the bobbin 32.

The probe 50 includes a shock receiving portion 52 and a shock transferring portion 56. The shock receiving portion 52 has a first end 51 and a flanged end 54. A substantial portion of the shock receiving portion 56 is positioned inside the sleeve 28 formed in the housing 10. The shock receiving portion 56 is positioned so that the first end 51 is proximate the hammer and the flanged end 54 is situated adjacent the threaded portion 20 of the housing 10.

As shown in FIG. 1, the shock transferring portion 56 is generally fused within the shock receiving portion 52 and has a second end 53 that extends out of the housing 10. A sleeve 58 is disposed over the flanged end 54 of the shock transferring portion and a cap 60 is disposed over the shock transferring portion 56 and screwed to the threaded portion 20 of the housing. The cap 60 and sleeve 58 cooperate to retain the probe 50 within the housing 10. In an alternative embodiment, instead of a probe 50 a transfer member 50 such as a flat plate disposed against or formed in the exit end of the housing 10 could be used to transfer a shock wave. In a preferred embodiment the probe is made of stainless steel.

A power source 70 is attached to the lithotriptor 1 to supply energy to the coil 19. In a preferred embodiment the power source 70 is a battery. Alternatively, the power source may be a transformer, rectifier and a capacitor storage circuit. In another alternative embodiment the power source may be an external power source such as a pulse generator. Although larger power supplies may clearly be used to operate the device. One of the advantages with the present device is that relatively low amounts of power are required to operate the device. Thus, by way of example and without limitation a power source that is capable of supplying 150–2000 volts may be used to operate the device. Further, as examples but not limited to power sources of about 12 volts may be used, power sources of about 12–57 volts may be used, power sources having about 59 volts may be used, power sources having about 40 volts may be used, power sources having about 20 volts may be used, power sources having about 15 volts may be used, power sources having 10 volts may be used and power sources having about 5 volts may be used.

An actuator 80 is attached to the lithotriptor. In a preferred embodiment, the actuator is a push button 80 that may be pressed by the operating physician to supply current to the coil 19 of the voice coil. Alternatively, the actuator 80 may be a foot pedal, or a panel switch. Alternatively, the actuator may have the ability to regulate or control the amount of force with which the hammer strikes the probe. Such a variable control actuator may be, by way of example, a potentiometer.

The operation of a preferred embodiment of the present invention will now be described with reference to FIGS. 1 and 2. First the probe 50 is placed against a stone 90 and the bobbin 32 is in the position shown in FIG. 1. Next, a first magnetic field is provided by the presence of the permanent magnet 30; the first magnetic field is generally oriented towards the exit end 12 of the device. Energy is then supplied to the coil 19 of the voice coil to generate a second magnetic field that is generally oriented opposite to the first magnetic field. The resultant force created by the opposing forces of the first magnetic field and the second magnetic field propels the bobbin 32 and thereby the hammer 40, from the right to the left (as viewed from FIGS. 1 and 2), to the position shown in FIG. 2. In this position, the hammer strikes the probe 50 and the kinetic energy of the bobbin 32 is transferred to the cup 42, then the kinetic energy is transferred from the cup 42 to the hammer 40 and finally the kinetic energy is transferred to the probe 50, thus producing a shock wave in the probe 50. The shock wave propagates along the probe 50 to the second end 53 where it is transferred to the stone 90 and thereby crushes the stone 90.

The movement of the bobbin 32 from the first position to the second position causes the spring 62 to compress. After the bobbin reaches the second position shown in FIG. 2 and the energy to the coil is stopped, the compressed spring 62 creates a force that directs the bobbin 32 from left to right (as viewed from FIGS. 1 and 2) to the first position, shown in FIG. 1.

In use, the physician positions the lithotriptor using a endoscope (not shown) such that the second end 53 of the probe 50 contacts a stone 90 or calculus within the body that the physician wishes to crush. The physician provides a current to the coil 19 of the voice coil by using an actuator 80 to actuate the power source 70. This results in the operation described above that produces a shock wave that crushes the stone 90. The bobbin 32 then returns to the first position and the physician can then repeat the foregoing steps to destroy multiple stones.

Figure 3:
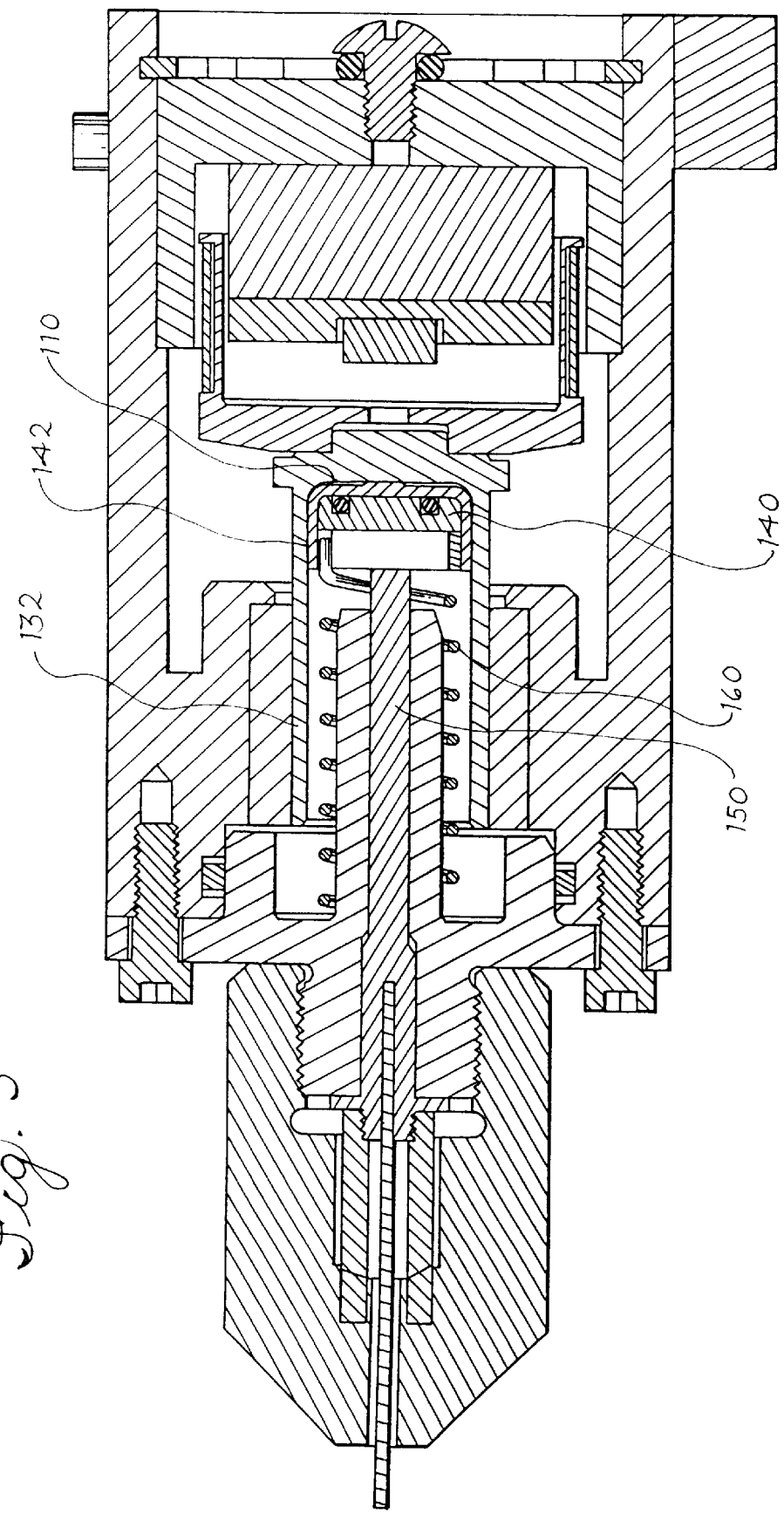
FIG. 3 is a cross sectional view of an embodiment of the present invention.

Referring to FIGS. 3–4, a second preferred embodiment of a lithotriptor 1 of the present invention is shown. The device is generally the same as the lithotriptor of FIGS. I and 2 and the similar elements have similar reference numbers. The primary difference between the preferred embodiment and the second preferred embodiment is that in the second embodiment, a biasing apparatus or o-ring 110 is positioned between the hammer 140 and the cup 142. Grooved openings 141 are cut into the hammer 140 and are sized and shaped to accept the o-ring 110. As a result of the positioning of the o-ring 110, the hammer 140 is not touching the cup 142 and in fact a gap 112 is formed between the hammer 140 and the cup 142. The o-ring 110 biases the hammer 140 away from the cup 142. Alternatively, the biasing apparatus could be a spring or an elastomeric pad.

A retainer 116 is positioned against the first wall 146 of the cup 142. The retainer 116 is preferably cylindrical shaped and is rectangular shaped in cross section (as viewed from FIGS. 3–4). The retainer is preferably a metal piece that is secured to the first wall 146 and holds the hammer 140 in position.

In operation, when energy is applied to the coil the bobbin 132 moves to the left (as viewed from FIG. 3) and the hammer 140 strikes the probe 150. Upon impact, kinetic energy is transferred from the bobbin 132 to the cup 142, then to the o-ring 110 and finally to the hammer 140. The presence of the o-ring creates a time lag in the kinetic energy transfer.

In another alternative embodiment of the invention (not shown), the device is generally the same as the device shown in FIGS. 1 and 2, however, the bobbin does not include a top member. Instead a biasing member is inserted inbetween the first portion and the second portion of the bobbin. In operation, when energy is applied to the coil the bobbin moves to the left (as viewed from FIG. 3) and the hammer 140 strikes the probe 150. Upon impact, kinetic energy is transferred from the first portion of the bobbin, to the biasing member, to the second portion of the bobbin and finally to the hammer. The presence of the biasing member creates time lag in the kinetic energy transfer. In a preferred embodiment the biasing member may be a belleville spring, a disc spring or a garter spring.

In another alternative embodiment of the invention (not shown), the device is generally the same as the device shown in FIGS. 1 and 2, however, the voice coil assembly does not include a hammer. Instead a biasing member is preferably attached to the bobbin member. Additionally a sleeve member substantially surrounds the transfer member. In operation, upon applying a current to the coil the bobbin member moves toward the probe and the biasing member contacts the sleeve and is compressed, thereby resulting in potential energy being stored within the biasing member. When the current is stopped, the biasing member releases and impacts against the transfer member thereby resulting in a shock wave being transmitted through the transfer member that may be used to crush a stone. In a preferred embodiment the biasing member is comprised of a pair of leaf springs operatively attached to the bobbin member.

An advantage of the present invention is that generally a lesser amount of energy is required to operate the device as compared to prior art devices. The fact that the present invention requires less energy to operate than prior art devices provides several advantages.

First, the lower energy requirement allows the present invention to utilize a portable power source, such as a battery. This eliminates the necessity of having a cord running from the device to an external power source.

In addition, an important advantage from the foregoing design is that modifying the speed at which the bobbin 32 impacts the probe 50 is easier to accomplish than in prior art designs. The speed and therefore the impact force of the hammer can be better controlled because the device does not require saturating an electromagnetic mass body to cause it to move but instead requires passing relatively small amounts of energy through the coil disposed around the bobbin.

Further producing a first magnetic field without a permanent magnet would require a significant amount of coil that would have to be insulated. The need for this additional insulation would increase the cost of the product. Thus, the present invention is generally more cost efficient to manufacture than the prior art.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A device for producing a shock wave to impact an object, comprising:
   a transfer member;
   a voice coil assembly comprising a permanent magnet and a bobbin member, wherein the permanent magnet provides a first magnetic field; and,
   a coil operatively attached to the bobbin member, wherein when a voltage is applied to the coil a second magnetic field is generated that opposes the first magnetic field and thereby propels the bobbin member to contact the transfer member to cause a shock wave to travel along the transfer member.

2. The device of claim 1, wherein the bobbin member is comprised of a non-magnetic material.

3. The device of claim 1, wherein the transfer member is a probe.

4. The device of claim 1, further comprising a power source operatively attached to the device.

5. The device of claim 4, wherein the power source is a battery.

6. The device of claim 1, wherein a portion of the bobbin member is disposed around the permanent magnet when the bobbin member is in a first position.

7. A device for producing a shock wave to impact an object, comprising:
   a transfer member;
   a voice coil assembly comprising a permanent magnet that provides a first magnetic field, a bobbin member, and a hammer comprised of a non-magnetic material to contact the transfer member; and
   a coil operatively attached to the bobbin member, wherein when a voltage is applied to the coil a second magnetic field is generated that opposes the first magnetic field and thereby propels the bobbin member to contact the transfer member to cause a shock wave to travel along the transfer member.

8. The device of claim 7, further comprising a cup positioned inbetween and operatively attached to the bobbin member and the hammer.

9. The device of claim 8, further comprising an O-ring positioned between the hammer and the cup.

10. A device for producing a shock wave to impact an object, comprising:
    a transfer member;
    a voice coil assembly comprising a permanent magnet and a bobbin member, wherein the permanent magnet provides a first magnetic field;
    a coil operatively attached to the bobbin member, wherein when a voltage is applied to the coil a second magnetic field is generated that opposes the first magnetic field and thereby propels the bobbin member to contact the transfer member to cause a shock wave to travel along the transfer member; and
    a biasing member to bias the bobbin member in a first position.

11. A device for producing a shock wave to impact an object, comprising:
    a housing having an exit end;
    a transfer member operatively attached to the exit end of the housing;
    a bobbin member, wherein the bobbin member is movable; and
    a hammer operatively attached to the bobbin member and movable from a rest position to a second position, wherein when the hammer is in the second position the hammer impacts the transfer member to produce a shock wave that travels along the transfer member.

12. The device of claim 11, wherein the bobbin member is comprised of a non-magnetic material.

13. The device of claim 11, wherein the transfer member is a probe.

14. The device of claim 11, comprising a coil attached to the bobbin member, wherein when a voltage is applied to the coil a magnetic field is generated.

15. The device of claim 11, comprising a coil attached to the bobbin member, wherein when a voltage is applied to the coil a magnetic field is generated.

16. A device for producing a shock wave to impact an object, comprising:
    a housing having an exit end;
    a transfer member operatively attached to the exit end of the housing;
    a hammer movable from a rest position to a second position, wherein the hammer is comprised of a non-magnetic material and when the hammer is in the second position the hammer impacts the transfer member to produce a shock wave that travels along the transfer member; and a battery to power the device.

17. A device for producing a shock wave to impact an object, comprising:
    a housing having an exit end;
    a transfer member operatively attached to the exit end of the housing;
    a hammer operatively attached to a bobbin member and movable from a rest position to a second position, wherein when the hammer is in the second position the hammer impacts the transfer member to produce a shock wave that travels along the transfer member;
    a battery to power the device; and
    a cup positioned inbetween and operatively attached to the bobbin member and the hammer.

18. The device of claim 17, further comprising an o-ring positioned between the hammer and the cup.

19. The device of claim 17, wherein the bobbin member is movable.

20. The device of claim 19, comprising a coil attached to the bobbin member, wherein when a voltage is applied to the coil a magnetic field is generated.

21. The device of claim 17, comprising a coil attached to the bobbin member, wherein when a voltage is applied to the coil a magnetic field is generated.

22. A device for producing a shock wave to impact an object, comprising:
    a housing having an exit end;
    a transfer member operatively attached to the exit end of the housing;
    a hammer operatively attached to a bobbin member and movable from a rest position to a second position, wherein when the hammer is in the second position the hammer impacts the transfer member to produce a shock wave that travels along the transfer member;
    a battery to power the device; and
    a biasing member to bias the bobbin member in a first position.

23. The device of claim 22, wherein the bobbin member is movable.

24. The device of claim 23, comprising a coil attached to the bobbin member, wherein when a voltage is applied to the coil a magnetic field is generated.

25. The device of claim 22, comprising a coil attached to the bobbin member, wherein when a voltage is applied to the coil a magnetic field is generated.

26. A device for producing a shock wave to impact an object, comprising:

a housing having an exit end;

a transfer member operatively attached to the exit end of the housing;

a permanent magnet disposed within the housing opposite the exit end to provide a first magnetic field;

a magnetic field generating member spaced apart from the permanent magnet; and a hammer fixed with the magnetic field generating member, the magnetic field generating member operative to provide a second magnetic field that opposes the first magnetic field to propel the hammer to strike the transfer member thereby causing a shock wave to travel along the transfer member.

27. The device of claim 26, wherein the magnetic field generating member is comprised of a non-magnetic material.

28. The device of claim 26, wherein the hammer is comprised of a non-magnetic material.

29. The device of claim 26, further comprising a cup positioned inbetween and operatively attached to a bobbin member and the hammer.

30. The device of claim 29, further comprising a biasing apparatus positioned between the hammer and the cup.

31. The device of claim 30, wherein the biasing apparatus is an o-ring.

32. The device of claim 26, wherein the transfer member is a probe.

33. The device of claim 26, further comprising a biasing member to bias the magnetic field generating member in a first position.

34. The device of claim 26, further comprising a power source operatively attached to the device.

35. The device of claim 34, wherein the power source is a battery.

36. The device of claim 26, wherein the magnetic field generating member is a bobbin.

37. A device for producing a shock wave to impact an object, comprising:

a housing having a magnet end and an exit end, the exit end defining an opening;

a probe attached to the housing and extending through the opening;

a permanent magnet disposed within the housing proximate the magnet end;

a bobbin member located intermediate the permanent magnet and the probe; the bobbin member movable between a first position and a second position;

a coil operatively attached to a portion of the bobbin member; and a hammer positioned intermediate the bobbin and the probe, wherein passing an electrical current through the coil results in the bobbin member moving from a first position to a second position causing the hammer to strike the probe, thereby causing a shock wave to travel through the probe.

38. The device of claim 37, wherein the bobbin member is comprised of a non-magnetic material.

39. The device of claim 37, wherein the hammer is comprised of a non-magnetic material.

40. The device of claim 37, further comprising a cup positioned inbetween and operatively attached to the bobbin member and the hammer.

41. The device of claim 40, further comprising an o-ring positioned between the hammer and the cup.

42. The device of claim 37, further comprising a biasing member to bias the bobbin member in a first position.

43. The device of claim 37, further comprising a power source operatively attached to the device.

44. The device of claim 43, wherein the power source is a battery.

45. A device for producing a shock wave to impact an object, comprising:

means for transferring a shock wave to an object;

means for providing a first magnetic field;

means for generating a second magnetic field to oppose the first magnetic field; and means for impacting the means for transferring, the means for impacting being operatively attached to the means for generating so that when the second magnetic field is generated the means for impacting strikes the means for transferring to produce a shock wave.

46. A method for producing a shock wave, comprising:

providing a transfer member;

providing a voice coil assembly including a permanent magnet and a bobbin member;

providing a first magnetic field providing a hammer attached with the bobbin member;

providing a coil operatively attached to the bobbin member; and applying a voltage to the coil to generate a second magnetic field that opposes the first magnetic field thereby propelling the hammer to strike the transfer member.

* * * * *